US006808711B2

(12) United States Patent
Motz et al.

(10) Patent No.: US 6,808,711 B2
(45) Date of Patent: Oct. 26, 2004

(54) **IMMUNOLOGICALLY ACTIVE PROTEINS FROM *BORRELIA BURGDORFERI*, NUCLEIC ACIDS WHICH ENCODE THEM, AND THEIR USE IN TEST KITS AND AS VACCINES**

(75) Inventors: Manfred Motz, München (DE); Erwin Soutschek, Berg (DE)

(73) Assignee: Mikrogen Molekularbiologische Entwicklungs-GmbH, Munich (DE)

( * ) Notice: Subject to any disclaimer, the term of this patent is extended or adjusted under 35 U.S.C. 154(b) by 0 days.

(21) Appl. No.: 10/403,220

(22) Filed: Mar. 26, 2003

(65) Prior Publication Data

US 2003/0185859 A1 Oct. 2, 2003

Related U.S. Application Data

(62) Division of application No. 09/242,299, filed as application No. PCT/EP97/04215 on Aug. 1, 1997, now Pat. No. 6,610,301.

(30) Foreign Application Priority Data

Aug. 14, 1996 (DE) ......................................... 196 32 862

(51) Int. Cl.$^7$ ......................... A61K 39/02; G01N 33/53; G01N 33/966; C07H 21/04

(52) U.S. Cl. ...................... 424/190.1; 424/9.1; 424/9.2; 424/184.1; 424/185.1; 424/200.1; 424/234.1; 435/9; 435/69.1; 530/300; 530/350; 536/23.1; 536/23.7

(58) Field of Search ...................... 424/9.1, 9.2, 184.1, 424/185.1, 190.1, 200.1, 234.1; 435/6, 69.1; 530/300, 350; 536/23.1, 23.7

(56) References Cited

U.S. PATENT DOCUMENTS

| 5,246,844 A | 9/1993 | Norris et al. ............. 435/172.3 |
| 5,279,938 A | 1/1994 | Rosa ............................. 435/6 |
| 5,470,712 A | 11/1995 | Simpson et al. ........... 435/7.32 |

FOREIGN PATENT DOCUMENTS

| DE | 3942728 | 5/1991 | ............ C07K/15/04 |
| DE | 4018988 | 12/1991 | ............ C07K/15/04 |
| EP | 0643974 | 9/1990 | .......... A61K/39/02 |
| EP | 0418827 | 3/1991 | .......... A61K/39/40 |
| EP | 0540457 | 10/1992 | ............ C12Q/1/68 |
| EP | 0565208 | 10/1993 | ............ C07K/15/00 |
| WO | WO-91/13630 | 9/1991 | .......... A61K/39/00 |
| WO | WO-93/04175 | 3/1993 | ............ C12N/15/31 |
| WO | WO-94/19488 | 9/1994 | ............ C12Q/1/68 |
| WO | WO-94/20536 | 9/1994 | ............ C07K/13/00 |
| WO | WO-95/04145 | 2/1995 | ............ C12N/15/31 |
| WO | WO-95/09919 | 4/1995 | ............ C12N/15/30 |
| WO | WO-95/12676 | 5/1995 | ............ C12N/15/31 |
| WO | WO-95/35379 | 12/1995 | ............ C12N/15/32 |
| WO | WO-96/05313 | 2/1996 | ............ C12N/15/31 |
| WO | WO-96/34106 | 10/1996 | ............ C12N/15/30 |
| WO | WO-97/27301 | 7/1997 | ............ C12N/15/30 |

OTHER PUBLICATIONS

Caporale, D., et al., "Sequence Variation in the Outer–Surface–Protein Genes of *Borrelia burgdorferi*", *Molecular Biology and Evolution*, 11, Abstract Only, (Jan. 1994), 51–64.

Coleman, James, et al., "Variations in the ospB Gene of *Borrelia burgdorferi* Result in Differences in Monoclonal Antibody Reactivity and in Production of Escape Variants", *Infection and Immunity*, 62, Abstract Only, (Jan. 1994), 303–307.

Guo, B., et al., Sequence Listing, Decoring Binding Protein B., EMBL Database, Accession No. 006877, (Sep., 1995), 1 p.

Guo, B., et al., "Adherence of *Borrelia burgdorferi* to the Proteoglycan Decorin", *Infection and Immunity*, 63, (Sep., 1995), 3467–3472.

Guo, Betty, et al., "Evidence that the Decorin Binding Protein of *Borrelia burgdorferi* is an Adhesin", *Abstracts of the General Meeting of the American Society for Microbiology*, 96, D–38, (May 1996), 248.

Guo, B., et al., "Identification of Decorin Binding Proteins on the Outer Membrane Surface of *Borrelia burgdorferi*", *Abstracts of the General Meeting of the American Society for Microbiology*, 94, D–161, (May 1994), 124.

(List continued on next page.)

*Primary Examiner*—Rodney P Swartz
(74) *Attorney, Agent, or Firm*—Schwegman, Lundberg, Woessner & Kluth, P.A.

(57) ABSTRACT

The present invention relates to immunologically active proteins from *Borrelia burgdorferi* which are present in a form which is free of other proteins derived from *Borrelia burgdorferi* and which exhibit the sequence of the protein 1829-22A, which has the amino acid sequence (SEQ. ID NO:1)
MKKFNLIIEALFAILLTACNFGLMEETKIALESSSKDVKNKILQIKKDAE

DKGVNFAAFTSSETGSKVTNGGLALREAKIQAINEVEKFLKRIEEEALKL

KEHGNSGQFLELFDLLLEVLESLEPIGIKGLKDFISEEAKCNPISTSER

LIEVKVQIENKMEEVKRKQNLNKERKSNKGKKKK or a part sequence therefor having at least 10 consecutive amino acids, or exhibit the sequence of the protein 1829-22B, which has the amino acid sequence (SEQ. ID NO:2)
MIKYNKIILTLTLLASLLAACSLTGKARLESSVKDITNEIEKAIKEAEDA

GVKTDAFTETQTGGKVAGPKIRAAKIRVADLTIKFLEATEEETITFKENG

AGEDEFSGIYDLILNAAKAVEKIGMKDMTKTVEEAAKENPKTTANGIIEI

VKVMKAKVENIKEKQTKNQK or part sequence thereof having at least 10 consecutive amino acids.

8 Claims, 4 Drawing Sheets

OTHER PUBLICATIONS

Hughes, C., et al., "Protective Immunity is Induced by a *Borrelia burgdorferi* Mutant that Lacks OspA and OspB", *Infection and Immunity, 61*, Abstract Only,(Dec. 1993), 5115–22.

Marconi, R., et al., "Variability of osp Genes and Gene Products Among Species of Lyme Disease Spirochetes", *Infection and Immunity, 61*, Abstract Only, (Jun. 1993), 2611–7.

Shoberg, R., et al., "Identification of a Highly Cross–Reactive Outer Surface Protein B Epitome Among Diverse Geographic Isolates of Borrelia Causing Lyme Disease", *Journal of Clinical Microbiology, 32*, Abstract Only, (Feb. 1994), 489–500.

Wilske, B., et al., "Antigenic Variation and Strain Heterogeneity in Borrelia", *Research In Microbiology, 143*, Abstract Only, (Jul.–Aug. 1992), 583–96.

Wilske, B., et al., "Immunological and Molecular Polymorphisms of OspC, and Immunodominant Major Outer Surface Protein of *Borrelia burgdorferi*", *Infection and Immunity, 61*, Abstract Only, (May 1993), 2182–91.

Fig. 1: DNA sequence 1829-22B

```
5' ATGATTAAATATAATAAAATTATACTTACACTAACTTTACTTGCTAGCCT
GTTAGCAGCATGTAGTTTAACAGGAAAAGCTAGATTGGAATCATCAGTTAAAGACATTACAA
ATGAAATAGAGAAAGCTATAAAAGAAGCTGAAGACGCTGGTGTAAAGACAGACGCGTTCACA
GAAACACAAACAGGTGGCAAGGTGGCAGGCCCTAAAATAAGAGCAGCAAAAATACGCGTCGC
TGACTTAACAATCAAATTCCTAGAAGCAACAGAAGAGGAAACTATTACATTTAAAGAAAATG
GAGCGGGGAAGATGAATTCTCAGGAATATACGATTTAATACTCAACGCCGCAAAAGCAGTA
GAAAAAATTGGGATGAAAGATATGACAAAAACGGTCGAAGAGGCCGCTAAAGAAAATCCTAA
AACTACAGCTAATGGGATAATTGAGATTGTAAAAGTAATGAAAGCAAAAGTGGAAAACATTA
AAGAAAAACAAACTAAAAATCAAAAATAA 3'
```

Fig. 2: Amino acid sequence 1829-22B

MIKNYKIILTLTLLASLLAACSLTGKARLESSVKDITNEIEKAIKEAEDAGVKTDAFTETOTGGK
VAGPKIRAAKIRVADLTIKFLEATEEETITFKENGAGEDEFSGIYDLILNAAKAVEKIGMKDMTK
TVEEAAKENPKTTANGIIEIVKVMKAKVENIKEKQTKNQK

Fig. 3: DNA sequence 1829-22A

```
5' ATGAAAAAGTTCAATTTAATAATTGAGGCGCTGTTTGCTATTCTATTAACAGCTTGTAATTTT
GGATTAATGGAAGAAACAAAAATAGCGCTTGAATCATCCTCTAAGGATGTAAAAAATAAAATTTT
ACAAATAAAAAAAGACGCTGAGGACAAGGGTGTAAATTTTGCAGCTTTTACAAGCAGTGAAACCG
GTTCTAAAGTGACAAATGGAGGATTAGCTTTAAGAGAAGCAAAAATACAAGCAATTAATGAAGTG
GAAAAGTTTCTCAAGAGAATAGAAGAAGAGGCTTTAAAACTTAAAGAACATGGAAATAGTGGTCA
ATTCTTGGAGCTGTTTGACTTACTGCTTGAAGTTTTAGAATCATTAGAACCGATTGGAATAAAAG
GCTTAAAAGACTTTATTTCAGAGGAAGCTAAATGTAACCCTATAAGCACATCTGAAAGATTAATT
GAGGTTAAGGTGCAAATAGAAAATAAGATGGAAGAGGTTAAGAGAAAACAAAATCTTAATAAGGA
GAGAAAAAGTAATAAAGGCAAAAAAAAG
AAATAA 3'
```

Fig. 4: Amino acid sequence 1829-22A

MKKFNLIIEALFAILLTACNFGLMEETKIALESSSKDVKNKILQIKKDAEDKGVNFAAFTSSETG
SKVTNGGLALREAKIQAINEVEKFLKRIEEEALKLKEHGNSGQFLELFDLLLEVLESLEPIGIKG
LKDFESEEAKCNPISTSERLIEVKVQIENKMEEVKRKQNLNKERKSNKGKKKK.

IMMUNOLOGICALLY ACTIVE PROTEINS FROM *BORRELIA BURGDORFERI*, NUCLEIC ACIDS WHICH ENCODE THEM, AND THEIR USE IN TEST KITS AND AS VACCINES

CROSS-REFERENCE TO RELATED APPLICATIONS

This application is divisional application of U.S. patent application Ser. No. 09/242,299 filed on Feb. 12, 1999 now U.S. Pat. No. 6,610,301, which in turn is a 371 filing of International Patent Application No. PCT/EP97/04215, filed on Aug. 1, 1997, which in turn is an international filing of German Patent Application No. 19632862.4, filed on Aug. 14, 1996, which applications are incorporated herein by reference.

Lyme borreliosis is the most frequent of the infectious diseases of humans which are transmitted by ticks. A substantial proportion of the ticks which serve as vectors for transmitting Lyme borreliosis are infected with the pathogen of Lyme *borreliosis*, i.e. the spirochete *Borrelia burgdorferi*. Depending on the geographic region, the percentage infected can vary from 1% up to 100%.

An infection with *B. burgdorferi* leads to a complex clinical picture, which can be subdivided into different stages.

In some cases, the infection with *B. burgdorferi* can take a subclinical course. However, late sequelae, which are caused by unrecognized or untreated Borrelia infections, frequently present a problem. Particularly because of the dangerous diseases, such as carditis, myositis, iritis, panophthalmitis or neurological manifestations, which can occur when infections are not recognized or not treated, it is important to be able to diagnose a possible infection with *B. burgdorferi* as reliably and accurately as possible.

The pathogen can be detected in patient material, in particular in the early stages. However, it is disadvantageous in this context that culturing *B. burgdorferi* is relatively difficult and therefore as a rule left to specialist laboratories.

It is desirable, therefore, to detect the antibodies in serum and also in cerebrospinal fluid, in the case of neurological manifestations, and in joint aspirates in the case of joint ailments.

For diagnosis, it is important to be able to decide whether an infection only occurred recently, or whether the infection is one which took place some while ago. This distinction can be made immunologically determining the nature of the detected antibodies; as a rule, IgM antibodies suggest that the infection only occurred recently whereas IgG antibodies suggest that the infection took place some while ago.

It is also important for diagnosis that the diagnostic tests are specific, i.e. that no cross-reactions occur with those bacterial pathogens, such as *Treponema pallidum*, which are to certain degree phylogenetically related to the borrelias.

On the other hand, however, it is also of importance for diagnosis that, if at all possible, all the strains of *Borrelia burgdorferi* can be recognized by the proteins or peptides which are employed in the test method.

Since Lyme borreliosis is widespread and since an infection can readily be transmitted by means of tick bite, there is also a substantial need to develop vaccines which ensure immune protection against borrelia infections.

Those proteins which, on the surface of the bacteria, come into contact with the immune system of the infected organism are particularly suitable for developing vaccines.

Two proteins have now been found, within the context of the present invention, which are particularly suitable both for diagnosis and for developing vaccines.

The present invention relates, therefore, to immunologically active proteins from *Borrelia burgdorferi* which are present in a form which is free of other proteins derived from *Borrelia burgdorferi* and which exhibit the sequence of the protein 1829-22A, having the amino acid sequence (SEQ ID NO:1)

MKKFNLIIEALFAILLTACNFGLMEETKIALESSSKDVKNKILQIKKDAE

DKGVNFAAFTSSETGSKVTNGGLALREAKIQAINEVEKFLKRIEEEALKL

KEHGNSGQFLELFDLLLEVLESLEPIGIKGLKDFISEEAKCNPISTSERL

IEVKVQIENKMEEVKRKQNLNKERKSNKGKKKK or a part sequence thereof having at least 10 consecutive amino acids, or the sequence of the protein 1829-22B, having the amino acid sequence (SEQ ID NO:2)

MIKYNKIILTLTLLASLLAACSLTGKARLESSVKDITNEIEKAIKEAEDA

GVKTDAFTETQTGGKVAGPKIRAAKIRVADLTIKFLEATEEETITFKENG

AGEDEFSGIYDLILNAAKAVEKIGMKDMTKTVEEAAKENPKTTANGIIEI

VKVMKAKVENIKEKQTKNQK or a part sequence thereof having at least 10 consecutive amino acids.

In accordance with the invention, preference is given to using those part sequences which possess epitopes which are diagnostically and/or therapeutically relevant. In the case of protein 1829-22A, whose sequence is given in the sequence listing under SEQ ID NO:1, the following part sequences are particularly preferred: the region between amino acid 31 (Lys) and amino acid 55 (Asn). Another preferred polypeptide is located between position 60 (Thr) and position 71 (Gly). A further preferred polypeptide is located between amino acid 82 (Gln) and amino acid 108 (Gln). The C-terminal region between amino acid 130 (Gly) and amino acid 183 (Lys) is also particularly preferred.

In the case of protein 1829-22B, which is represented by Seq. ID No. 2, the following part regions are particularly preferred: amino acid 61 (Gln) to amino acid 71 (Ile); amino acid 87 (Glu) to amino acid 108 (Gly); amino acid 121 (Glu) to amino acid 145 (Asn), and the C-terminal region from amino acid 150 (Ile) to amino acid 170 (Lys). The positions of the amino acids are given in the sequence listings. The peptides which exhibit the abovementioned part sequences can either be prepared by means of chemical synthesis or be expressed recombinantly in suitable host systems.

The proteins or peptides according to the invention may be prepared by means of recombinant methods, which has the advantage that no other proteins derived from *B. burgdorferi* are associated with the desired proteins. Alternatively, suitable peptides may also be synthesized in the classical chemical maimer. Such peptides are also free of immunologically inactive impurities. However, it is entirely possible to employ the proteins or peptides according to the invention in test kits or in vaccines together with other proteins which have been isolated from *B. burgdorferi*.

The term immunologically active protein which is used within the context of the present invention, encompasses not only protein which comprises the complete amino acid sequence of protein 1829-22A or protein 1829-22B but also parts of these proteins which are at least long enough to encompass at least one linear epitope. In general, the minimum length of a peptide according to the invention which is able to exhibit the property of an epitope is at least 6, preferably 10, particularly preferably 25 and very particularly preferably at least 50 amino acids.

The fact must be taken into consideration that, in the individual strains of *Borrelia burgdorferi,* at least minor changes occur in the amino acid sequence of the protein, depending on the particular strain. The present invention therefore also relates immunologically active proteins or peptides which exhibit high degree of homology with the above-described amino acid sequences.

The immunologically active proteins or peptides according to the invention exhibit an homology of at least 60%, preferably at least 80% and particularly preferably at least 90%, based on proteins 1829-22A and 1829-22B according to the invention. The term homology of 90% is understood as meaning, for example, that, in the homologous peptide, 9 out of 10 amino acids are identical to the corresponding amino acids at the homologous sites in amino acid sequence 1829- 22A or amino acid sequence 1829- 22B.

Within the context of the present invention, those regions of the proteins or peptides according to the invention are particularly important which exhibit epitopes, that is sites in the protein to which antibodies bind specifically. Determining at which sites epitopes are to be expected can be either achieved using computer methods which are known per se, or it is also possible to synthesize defined short peptides having a length of at least 10, preferably at least 25, amino acids. These peptides are then tested with positive sera to determine whether immunological reactions do or do not take place. In this way, it is possible to identify linear epitopes. These proteins or peptides, can be made by recombinant methods, with the peptides, for example, being expressed in microorganisms as fusion proteins, or the peptides can be synthesized by means of classical synthesis (Merrifield technique).

Identifying immunologically relevant epitopes is important not only for diagnosis but also, in particular, for preparing vaccines. For vaccines, regions of the proteins according to the invention which are very reactive immunologically can be combined with appropriate regions of other, previously known proteins from *Borrelia burgdorferi,* such as OspA or OspC, or with flagellin amino acid sequences.

The present invention also relates to test kits for detecting antibodies against *Borrelia* strains which test kits contain at least one immunologically active protein according to the invention, which is able to react with the antibodies which are present in the fluid under investigation, and which contain at least one reporter component which makes it possible to detect complexes consisting of immunologically active protein and antibody.

Preference is given to test kits which contain at least one immunologically active protein having a part sequence of protein 1829-22A and at least one protein having a part sequence of protein 1829-22B.

The reporter component can be an antibody which is directed against the antibody to be detected and which exhibits label. In this context, the reporter component is preferably an anti-human IgG antibody or an anti-human IgM antibody. The label is frequently an enzyme which is able to catalyze a color reaction.

One detection possibility consists in the immunologically active protein according to the invention, or a monoclonal antibody which is directed against it, being biotinylated and the reporter component being avidin or streptavidin to which enzyme, in particular peroxidase, is covalently bonded.

In a preferred embodiment of the invention, the test kit is an ELISA test kit. In a particularly preferred embodiment of the present invention, at least one immunologically active protein according to the invention is coupled to microtiter plates, and the reporter component consists of anti-human immunoglobulin, in particular anti-IgG antibodies and/or anti-IgM antibodies, to which an enzyme which catalyzes a color reaction is coupled.

In another preferred embodiment of the present invention, the test kit is an immunoblot, which is also described as a protein blot or a western blot. In test kits of this nature, protein is transferred, using an electrophoresis gel, for example a polyacrylamide gel, onto an immobilizing matrix (e.g. nitrocellulose filter). The transfer can be effected, for example, by means of electrotransfer. An immunological reaction then takes place between the proteins present on the matrix and the antibodies which are directed against the proteins. The antibodies can then be detected by means of suitable methods, e.g. using enzyme-labeled anti-antibody antibodies.

The term "test kits" is understood as meaning a set of test reagents which makes it possible to detect particular antibodies. The test kits according to the invention contain, as the component according to the invention, at least one protein or peptide according to the invention. The immunologically active protein or peptide acts as an antigen and reacts with the antibodies which are present in the fluid under investigation. The test kits according to the invention can be based on various principles which are known per se. As rule, a reaction takes place between the antigen and antibodies and this reaction, or the complex which is formed in this context, is detected. It is possible for the antigen to be bound to a solid phase such as a microtiter plate or magnetic beads. This antigen can then be brought into contact with the fluid under investigation (serum or cerebrospinal fluid). The antibodies which are present in the fluid under investigation then bind to the antigen. A wash is then customarily performed and the bound antibodies are detected by means of anti-antibody antibodies which carry a label. The label can be a radioactive isotope or an enzyme which catalyzes a color reaction, for example horseradish peroxidase.

However, there are large number of test configurations which are known per se to the skilled person. Thus, the anti-antibody antibody can also, for example, be bound to a solid phase and the antigen can possess a detectable label.

Within the context of the present invention, preference is given, in particular, to those test kits which are suitable for implementing an ELISA (enzyme-linked immunosorbent assay) or for implementing a so-called Western blot.

Since the use of radioactively-labeled labeling substances is encountering ever increasing resistance, preference is given, according to the invention, to the complex, consisting of antigen/antibody to be detected and anti-antibody antibody, being detected by either the antigen or the anti-antibody antibody being biotinylated. The complex is then detected by adding avidin to which a color reaction-catalyzing enzyme, for example, is coupled.

Within the context of the present invention, particular preference is also given to the so-called $\mu$ capture test. In the $\mu$ capture test, an antibody against human IgM antibodies ($\mu$ chains) is bound to the solid phase. These anti-antibody antibodies capture both the antigen-specific and the nonspecific IgM antibodies from the serum mixture. After antigen, which can be directly labeled, has been added, the IgM immune response is detected. Alternatively, unlabeled antigen can also be employed, and the antigen (immunologically active protein according to the invention) is then detected using a further labeled antibody which is directed against the antigen. The label can, for example, be an enzyme which catalyzes a color reaction.

The immunologically active proteins or peptides according to the invention can also be used for preparing monoclonal antibodies. Monoclonal antibodies are prepared by means of standard methods which are known per se.

The present invention furthermore relates vaccines which contain at least one protein or peptide according to the invention. Consequently, the immunologically active proteins, according to the invention, from Borrelia burgdorferi can be used for preparing a vaccine for protecting against infections with Borrelia burgdorferi bacteria.

For preparing a vaccine, it is essential to identify those regions in immunologically active proteins which elicit the formation of protective antibodies. When the immunologically active proteins are administered to the organism which is to vaccinated, antibodies must be formed which are such that, in association with an infection with Borrelia burgdorferi, they bind to the invading bacteria and enable the invading bacteria to be destroyed by the body's own immune system. While the vaccines according to the invention are preferably used for vaccinating humans, they can also be used for vaccinating animals. It is especially useful to vaccinate animals which can be bitten by ticks and thereby be infected with Borrelia burgdorferi. Vaccination is particularly useful in the case of dogs and horses.

The present invention also relates to nucleic acids which encode the immunologically active proteins according to the invention.

In this context, the nucleic acid is preferably a nucleic acid which exhibits a DNA sequence which encodes protein 1829-22A and possesses the sequence (SEQ ID NO:3)

ATGAAAAAGTTCAATTTAATAATTGAGGCGCTGTTTGCTATTCTATTAAC

AGCTTGTAATTTTGGATTAATGGAAGAAACAAAAATAGCGCTTGAATCAT

CCTCTAAGGATGTAAAAAATAAAATTTTACAAATAAAAAAAGACGCTGAG

GACAAGGGTGTAAATTTTGCAGCTTTTACAAGCAGTGAAACCGGTTCTAA

AGTGACAAATGGAGGATTAGCTTTAAGAGAAGCAAAAATACAAGCAATTA

ATGAAGTGGAAAAGTTTCTCAAGAGAATAGAAGAAGAGGCTTTAAAACTT

AAAGAACATGGAAATAGTGGTCAATTCTTGGAGCTGTTTGACTTACTGCT

TGAAGTTTTAGAATCATTAGAACCGATTGGAATAAAAGGCTTAAAAGACT

TTATTTCAGAGGAAGCTAAATGTAACCCTATAAGCACATCTCAAAGATTA

ATTGAGGTTAAGGTGCAAATAGAAAATAAGATGGAAGAGGTTAAGAGAAA

ACAAAATCTTAATAAGGAGAGAAAAAGTAATAAAGGCAAAAAAAAGAAAT

AA or a part sequence thereof which encompasses at least 18 nucleotides.

In another embodiment, the nucleic acid is a nucleic acid which exhibits a DNA sequence which encodes protein 1829-22B and possesses the sequence (SEQ ID NO:4)

ATGATTAAATATAATAAAATTATACTTACACTAACTTTACTTGCTAGCCT

GTTAGCAGCATGTAGTTTAACAGGAAAAGCTAGATTGGAATCATCAGTTA

AAGACATTACAAATGAAATAGAGAAAGCTATAAAAGAAGCTGAAGACGCT

GGTGTAAAGACAGACGCGTTCACAGAAACACAAACAGGTGGCAAGGTGGC

AGGCCCTAAAATAAGAGCAGCAAAAATACGCGTCGCTGACTTAACAATCA

-continued
AATTCCTAGAAGCAACAGAAGAGGAAACTATTACATTTAAAGAAAATGGA

GCGGGGGAAGATGAATTCTCAGGAATATACGATTTAATACTCAACGCCGC

AAAAGCAGTAGAAAAAATTGGGATGAAAGATATGACAAAAACGGTCGAAG

AGGCCGCTAAAGAAAATCCTAAAACTACAGCTAATGGGATAATTGAGATT

GTAAAAGTAATGAAAGCAAAAGTGGAAAACATTAAAGAAAAACAAACTAA

AAATCAAAAATAA or a part sequence thereof which encompasses at least 18 nucleotides.

According to the invention, preference is also given to part sequences of the abovementioned sequences, which part sequences possess at least 30 and particularly preferably 50 nucleotides.

The nucleic acids and nucleic acid fragments according to the invention, and nucleic acid fragments which hybridize with them and which have a length of at least 12 nucleotides, can be employed for detecting an infection with Borrelia burgdorferi using the polymerase chain reaction.

The nucleic acids according to the invention are preferably DNA sequences. The DNA sequences according to the invention are required for preparing the immunologically active proteins, according to the invention, from Borrelia burgdorferi by means of recombinant methods. However, it is also particularly advantageous to employ part sequences of the sequences according to the invention for diagnostic methods, with the PCR method having become very widespread. Short fragments of the nucleic acids according to the invention, which fragments are able to hybridize with the complementary sequences in the sample under investigation, are synthesized for this purpose. Very small quantities of the sought-after nucleic acids are then amplified by means of the polymerase chain reaction (PCR) and subsequently detected.

Another preferred use of the nucleic acids according to the invention is DNA vaccination. In this use, the nucleic acids according to the invention, or parts thereof, are introduced into the host to immunized, in association with which the nucleic acid can either be present in naked form or in the form of plasmids or retroviral vectors. The DNA is then translated in the host organism and the translated gene products immunize the host.

The present invention is clarified by the following examples.

BRIEF DESCRIPTION OF THE DRAWINGS

FIG. 1 is the nucleotide sequence from Borrelia burgdorferi (SEQ ID NO:4) which encodes protein 1829-22B.

FIG. 2 is the amino acid sequence of the protein 1829-22B (SEQ ID NO:2), derived from Borrelia burgdorferi.

FIG. 3 is the nucleotide sequence of from Borrelia burgdorferi (SEQ ID NO:3) which encodes protein 1829-22A.

FIG. 4 is the amino acid sequence of the protein 1829-22A (SEQ ID NO:1), derived from Borrelia burgdorferi.

EXAMPLE 1

Determining Partial Sequences

A protein fraction was partially purified from lysates of B. burgdorferi, strain Pko, by means of extraction with N-octyl β-D-thioglucopyranoside, in which it was soluble, and subjected to further fractionation by means of SDS polyacrylamide gel electrophoresis. Antigens from the region of lower molecular weight (<30 kDa) were then transferred by Western blotting to glass fiber matrix, and the appropriate pieces containing *B. burgdorferi* antigens were cut out (in accordance with Eckerskorn et al., 1998, Eur. J. Biochem. 176:509–519, A new siliconized fiber as support for protein-chemical analysis of electroblotted proteins. One of these proteins which was obtained in this way was investigated more closely. Direct partial sequencing was not possible since the N terminus was not accessible to sequencing. The antigen was therefore cleaved in the gel and the peptides were subsequently extracted.

For this, the antigen was separated by means of SDS PAGE and the gel was then stained with Coomassie blue. After the protein bands had been located, the gel was destained with 10% acetic acid. The protein band, and a corresponding reference band without antigen but of the same size, were cut out and pressed and comminuted through a sieve (pores 30 μm×100 μm). The crushed gel was washed for 2 min with ½ conc. incubation buffer (12.5M Tris, 0.5M EDTA, pH 8.5), and centrifuged, after which the buffer was removed. The gel, which had been extracted in this way, was dried for 1 h in a vacuum centrifuge down to a residual water content of about 5% and a rubber-like consistency. Endoprotease LysC was dissolved in 400 μl of 12.5M Tris/HCl, pH 8.5 (enzyme:protein=1:10) and 0.1% lauryl maltositol was added. 200 μl were in each case added to the sample and the reference and the mixtures were incubated at 37° C. overnight in a heating block shaker. After that, the peptides were separated by reversed phase chromatography on an HPLC apparatus and the sequences of selected peptides were analyzed. N-Terminal degradation of the amino acids, and consequently determination of the sequence, was carried out in an automated Porton 3600 sequencer (Beckmann Instruments) in accordance with the method of Edman & Begg (1967, Eur. J. Biochem. 1, 80–91). The following peptides were obtained after sequencing:

```
                                        (SEQ ID NO:5)
AA1829-22B P11: T-D-A-F-T-E-T-Q-T-G-G-K

AA1829-22B P13: D-I-T-N-E-I-E-K         (SEQ ID NO:6)

(SEQ ID NO:7)
AA1829-22B P23: F-L-E-A-T-E-E-E-T-I-T-F-K
```

EXAMPLE 2

Preparing the Probes

The subsequently listed oligodeoxynucleotide sequences were deduced from the amino acid sequences obtained as described in Example 1. Since there are usually several codon possibilities for an amino acid, base variations at the corresponding sites in the oligonucleotide had also to be taken into consideration and incorporated in equimolar ratios during the synthesis. In order to avoid the base variations being too great, the frequency of the codons in gene sequences which were already known and characterized molecular-biologically, such as OspA, OspC and p100, was analyzed and used for preparing the deduced oligonucleotide sequences.

AA1829-22B—Oligodeoxynucleotide Sequences

The bases given in brackets and separated by Z ";" were incorporated in equimolar ratios during the synthesis (on a Pharmacia DNA synthesizer):

```
Primer 1829-22B p11 oligodeoxynucleotide sequence:
                                        (SEQ ID NO:8)
AC(A;T) GAT GC(T;A) TTT AC(T;A) GA(A;G) AC(A;T)

CAA AC(A;T) GG(T;A) GG(T;A) AA

Primer 1829-22B p13 oligodeoxynucleotide sequence:
                                        (SEQ ID NO:9)
GAT AT(A;T) AC(A;T) AA(C;T) GA(G;A) AT(A;T)

GA(G;A) AA

Primer 1829-22B p23 oligodeoxynucleotide sequence:
                                       (SEQ ID NO:10)
TTT TT(A;G) GA(G;A) GC(T;A) AC(A;T) GA(G;A)

GA(G;A) GA(G;A) AC(A;T) AT(A;T) AC(A;T) TTT
```

EXAMPLE 3

Finding the Coding Gene Fragment

The oligonucleotide sequences were used as probes and employed in Southern blots after having been labeled with digoxigenin in accordance with The DIG system User's Guide for Filter Hybridization, Boehringer Mannheim GmbH). For this, chromosomal DNA was isolated from *Borrelia burgdorferi* strain Pko using a customary method (see Maniatis: Molecular Cloning, A Laboratory Manual), cleaved enzymically with various restriction endonucleases and fractionated on agarose gel. After prior denaturation, the DNA was transferred from the agarose gels to nylon membranes (Southern blotting: in accordance with The DIG system User Guide for Filter Hybridization, Boehringer Mannheim GmbH). The hybridization was carried out in accordance with standard conditions (see above, Boehringer Mannheim GmbH). Bound oligodeoxynucleotides were detected immunologically using anti-digoxigenin antibodies to which alkaline phosphatase was coupled. Appropriate hybridizing bands were identified after staining. After preparative agarose gel electrophoresis, these identified bands were eluted from the gel, precipitated with EtOH, taken up in a suitable buffer and ligated to *E. coli* plasmids which were enzymically cleaved with appropriate restriction endonucleases. The DNA, which had thus been ligated, was inserted into competent *E. coli* cells, giving rise to transformed *E. coli* cells. The positive *E. coli* cells were separated from the negative cells after plasmid screening and restriction endonuclease cleavage of the resulting DNA and subsequent repeated hybridization with the digoxigenin (Boehringer Mannheim)-labeled primers (see above). Suitable clones were found by hybridization. A restriction map of a HindIII/HindIII DNA insert was constructed using restriction endonucleases which preferentially recognized hexamer sequences. Different DNA fragments were then subcloned and subsequently sequenced by automated sequencing after fluorescence labeling (Applied Biosystems, ABIPrism 377, Weiterstadt).

Following analysis of the resulting sequence with a computer program for DNA analysis (DNASTAR, Lasergene, London), several open reading frames were identified. Two of these reading frames exhibited typical signal sequences such as start of the reading frame with methionine or ribosome binding site at an appropriate distance upstream of the reading frame. One reading frame exhibited distinct sequence correspondence with the originally obtained peptide sequences and the primers which were deduced from them. This reading frame has the sequence depicted in FIG. 1. The amino acid sequence which is deduced from it is depicted in FIG. 2.

Protein 1829-22B is 170 amino acids in length. The corresponding peptide sequences, which were found during the primary characterization, are underlined in FIG. 2.

Surprisingly, a further gene was found on the above-described DNA fragment. The reading frame was designated 1829-22A. The DNA sequence is depicted in FIG. 3.

The protein 1829-22A, which is deduced from it, has, with a length of 183 amino acids, the sequence depicted in FIG. 4.

EXAMPLE 4
Preparing Clones for Expressing the 1829-22B Antigen

Expression clones were prepared proceeding from the complete reading frame for the 1829-22B gene. Both the entire reading frame and a truncated fragment were prepared in this context. The following oligonucleotide primers were used for preparing the sequences.

```
Primer 1:
5' GAG GGA TCC ATC ATG ATT AAA TAT AAT AAA ATT ATA C 3'    (SEQ ID NO:11)

Primer 2:
5' GAG GGA TCC ATC ATG AAA AGT TTA ACA GGA AAA GCT AG 3'   (SEQ ID NO:12)

Primer 3:
5' GGA CTG CAG GTC GAC TTA TTT TTG ATT TTT A GT TTG 3'     (SEQ ID NO:13)
```

In this context, the primer combinations Primer 1 and Primer 3, and Primer 2 and Primer 3 were used for preparing the complete sequence and the truncated sequence, respectively. Purified DNA from a clone containing the entire insert (1829-22B, 1829-22A and flanking sequences, HindIII/HindIII fragment) was used as the template DNA. The polymerase chain reaction (PCR) was carried out using the PCR-Core Kit (Boehringer Mannheim) in accordance with the manufacturer instructions. The reaction was carried out in a thermocycler using the following program:

Program:
A. Denaturation time at 94° C., 4 min.
B. 35 cycles "Cycle: 1.94° C., 1 min. 2.42° C., 1 min. 3.72° C., 1.5 min."
C. Elongation: 72° C., 5 min.

The amplificates were cleaved enzymatically using restriction endonuclease recognition sequences within the primer sequences and ligated into an E. coli plasmid, e.g. pUC8, which was likewise cleaved with the same restriction endonucleases. Positive clones were identified after transformation and analysis of the clones both by agarose gel electrophoresis of enzymically cleaved DNA and also by SDS polyacrylamide gel electrophoresis and Coomassie Blue staining or subsequent transfer to nitrocellulose and immunological detection. In this context, it emerged that the truncated fragment was markedly easier to prepare and that consequently it was also possible to achieve superior reactivity in Western blots when this fragment was used.

EXAMPLE 5
Purifying Recombinant *Borrelia burgdorferi* Antigen 1829-22B From *E. coli*

A clone containing the 1829-22B antigen (pMS 1829-22B) is inoculated into 100 ml of L-broth (containing 50 μl of ampicillin/ml) and left to grow overnight; the culture is then transferred into 900 ml of L-broth/ampicillin (2×concentrated yeast extract/2 ml of glycerol), with this culture being induced with 2 mM IPTG after approx. 1 h and shaken for a further 2–3 h.

After centrifuging at 8000 rpm for 10 min, the pellet is resuspended in 20 ml of lysis buffer (50 mM Tris-HCl, pH 7.5, 2 mM EDTA, 0.2 mM DTE, 0.1 mM PMSF; 0.4 mg of lysozyme/ml). After the mixture has been stirred at room temperature for 30 min, Triton-X 100 is added (final concentration, 0.1–0.2%). 10 μl of benzonase (Merck) are also added. The mixture is stirred at room temperature for a further 30 min. The suspension, which is now clear, is adjusted to 1 M NaCl using solid NaCl and stirred at 4° C. for a further 30 minutes.

After the mixture has been centrifuged at 15,000 rpm for 30 minutes and at 4° C., the 1829-22B antigen is present quantitatively in the supernatant. The pellet is discarded. The supernatant is dialyzed against 10 mM Tris-HCl, pH 7.0, and 2 mM EDTA, with the buffer being changed several times. After the supernatant has been centrifuged and/or filtered, it is loaded onto DEAE sepharose (Pharmacia), with the column being equilibrated with 50 mM Tris-HCl and mM EDTA, pH 70. When elution is carried out with 0 M NaCl, the antigen is present in the flowthrough. The first fractions can be discarded, while the remainder is collected and dialyzed, in a dialysis bag, against 50 mM MES (2-[N-morpholino]ethanesulfonic acid) buffer, pH 6.0. After centrifuging and filtering, the antigen is loaded onto a .s-sepharose fast flow (Pharmacia) column. The column is first of all washed with 0 M NaCl and then eluted with a gradient of from 0 to 1 M NaCl. The 1829-22B antigen elutes as a sharp peak at about 0.2 M NaCl. After having been dialyzed against 10 mM Tris-HCl, pH 7.5, the antigen can be used in a suitable test kit or an ELISA or Western blot.

EXAMPLE 6
Using Recombinantly Produced *B. burgdorferi* Antigen 1829-22B in Western Blots For this, purified antigen 1829-22B is separated in an SDS polyacrylamide gel electrophoresis and transferred to nitrocellulose. For this purpose, SDS polyacrylamide gels are prepared as follows. The SDS gels consist of a stacking gel and a resolving gel (in accordance with Laemmli, UK 1970, Cleavage structural proteins during assembly of the head bacteriphage T4, Nature 227, 680–685). The composition of the resolving gels is as follows: 15% acrylamide (Bio-Rad), 0.026% diallyltartramide (DATD, Bio-Rad) per percent acrylamide, 0.15% SDS, 375 mM Tris-HCl, pH 8.5, 0.14 mM ammonium peroxydisulfate (AMPER, Bio-Rad) and 0.035% N, N, N', N'-tetramethylethylenediamine (TEMED, Bio-Rad). Amper and TEMED were used in this context as free radical starters for the polymerization. 2-4 hours after polymerization, the stacking gel (3.1% acrylamide, 0.08% DATD, 0.1% SDS, 125 mM Tris-HCl, pH 7.0, 3 mM Amper and 0.05% TEMED) was poured above the resolving gel. The anode and cathode chambers were filled with identical buffer solution: 25 mM Tris base, 192 mM glycine and 0.1% SDS, pH 8.5. The antigen-containing sample was treated with the same volume of sample loading buffer (3% sucrose, 2% SDS, 5% mercaptoethanol, 20 mM Tris-HCl, pH 7.0, bromophenol blue), and the mixture was then heated at 100° C. for precisely 5 minutes and loaded onto the stacking gel. The electrophoresis was carried out at room temperature overnight using a constant current strength of 6 mA for gels of 20×15 cm in size. The antigens were then transferred to nitrocellulose (Schleicher and Schuell, Dassel).

For the protein transfer, the gel was located, together with the adjacent nitrocellulose, between Whatmann MM filter paper, conductive, 1 cm-thick foamed material and two carbon plates which conducted the current by way of platinum electrodes. The filter paper, the foamed material and the nitrocellulose were soaked thoroughly with blotting buffer (192 mM glycine, 25 mM tris base, 20% methanol, pH 8.5). The transfer was carried out at 2 mA/cm$^2$ for 2 h. Free binding sites on the nitrocellulose were saturated, at 37° C. for 1 h, with Cohen buffer (1 mg of Ficoll 400/ml, 1 mg of polyvinylpyrrolidone/ml, 16 mg of bovine serum albumin/ml, 0.1% NP40, 0.05% Bacto-gelatin in sodium borate buffer, pH 8. 2); (in accordance with the method of Cohen et al. Localisation and synthesis of antigenic determinant of herpes simplex virus glycoprotein ⁻D that stimulates the production of neutralizing antibodies. J. Virol. 49, 1984, 4183–4187). The blot strips were incubated with patient sera (dilution, 1:100 in 154 mM NaCl and 10 mM Tris-HCl, pH 7.5) at room temperature overnight.

After incubation with the serum, the blot was washed four times for in each case 15 minutes with TTBS (50 mM Tris-HCl, pH 7.5, 500 mM NaCl, 0.01% Tween 20). The blot strips were then incubated, at room temperature for 2 h, with peroxidase-coupled anti-human IgG immunoglobulin (DAKO, dilution 1:1000 in 154 mM NaCl and 10 mM Tris-HCl, pH 7.5) or anti-human, IgM immunoglobulin (DAKO, dilution 1:500 in 154 mM NaCl and 10 mM Tris-HCl, pH 7.5). After having been washed several times with TTBS, the blot strips were stained with 10 mg of diaminobenzidine/50 ml and 0.01% hydrogen peroxide in 50 mM Tris-HCl, pH 7.5. The staining was stopped with 1N sulfuric acid and the blot was washed with water until acid free and dried between filter paper.

The results obtained with characterized sera are summarized in Table 1:

TABLE 1

| Sera | IgG-reactive | IgM-reactive |
|---|---|---|
| Blood donors n = 94 | 0/94 | not determined |
| Blood donors n = 20 | 0/20 | 0/20 |
| Lyme Borreliosis patients (Stage 2/3) or IgG serology-positive n = 24 | 24/24 | not determined |
| Lyme Borreliosis patients (Stage 1) or IgM serology-positive n = 10 | not determined | 1/10 |

EXAMPLE 7

Demonstrating the Diagnostic Importance of the Recombinant Antigen 1829-22B

For the ELISA, recombinant *Borrelia burgdorferi* antigens, such as p100, OspC or p41/internal fragment, without or in combination with purified p1829-22B antigen, were coated, at 4° C. and overnight, onto polystyrene plates in carbonate buffer, pH 10.6. The microtiter plates were saturated with BSA solution. The serum incubation took place, at 37° C. for 1 hour, in PBS, 1% bovine serum albumin, pH 7.0 (dilution buffer) at dilution of 1+100. After the plates had been washed four times with PBS, 0.05% Tween 20, pH 7.0 (washing buffer), anti-human IgG peroxidase conjugate in dilution buffer was added at 37° C. for 30 min. After the plates had been washed a further four times with washing buffer, TMB substrate was added and the plates were incubated at room temperature for 30 min in the dark. The reaction was stopped with sulfuric acid and the immune staining was measured at 450 nm in photometer. The cut-off was set by measuring defined positive sera and negative sera.

The results obtained in the experiment are summarized in Table 2 below. The results demonstrate that it was possible to obtain more clear cut results by using the p1829-22B antigen according to the invention. It has particularly to be emphasized that several sera which proved to be positive in a confirmatory test using immunoblotting were classified as negative in an EIA (enzyme immunoassay) without p 1829-22B.

TABLE 2

| | | EIA with p1829-22B | | | |
|---|---|---|---|---|---|
| Confirmatory test | | positive | questionable | negative | n |
| (Immunoblot) | positive | 55 | 0 | 0 | 55 |
| | questionable | 3 | 0 | 0 | 3 |
| | negative | 6 | 2 | 22 | 30 |
| | n | 64 | 2 | 22 | 88 |
| | | EIA without p1829-22B | | | |
| Confirmatory test | | positive | questionable | negative | n |
| (Immunoblot) | positive | 43 | 4 | 8 | 55 |
| | questionable | 1 | 0 | 2 | 3 |
| | negative | 6 | 2 | 22 | 30 |
| | n | 50 | 6 | 32 | 88 |

What is claimed is:

1. A nucleic acid, which encodes an immunologically active *Borrelia burgdorferi* protein which is present in a form which is free of other proteins isolated from *Borrelia burgdorferi*, which protein exhibits the sequence of the protein 1829 -22A, having the amino acid sequence SEQ ID NO: 1 or a fragment thereof having at least 10 consecutive amino acids, or the sequence of the protein 1829-22B, having the amino acid sequence SEQ ID NO:2 or a fragment thereof having at least 10 consecutive amino acids.

2. A nucleic acid as claimed in claim 1, wherein the fragment of SEQ ID NO:1 or of SEQ ID NO:2 exhibits at least 25 consecutive amino acids.

3. A nucleic acid as claimed in claim 1, wherein the fragment of SEQ ID NO:1 or of SEQ ID NO:2 exhibits at least 50 consecutive amino acids.

4. A nucleic acid as claimed in claim 1, which exhibits the DNA sequence encoding protein 1829-22A, and having the sequence SEQ. ID NO:3 or a fragment thereof which encompasses at least 18 consecutive nucleotides.

5. A nucleic acid as claimed in claim 1, which exhibits a DNA sequence encoding protein 1829-22B and having the sequence SEQ ID NO:4 or a fragment thereof which encompasses at least 18 consecutive nucleotides.

6. A nucleic acid as claimed in claim 4, wherein the fragment encompasses at least 30 consecutive nucleotides.

7. A nucleic acid as claimed in claim 5, wherein the fragment encompasses at least 30 consecutive nucleotides.

8. A method for detecting an infection with *Borrelia burdorferi* in a patient comprising:

contacting a physiological sample from the patient with a nucleic acid sequence encoding an immunologically active *Borrelia burdorferi* protein which is present in a form which is free of other proteins isolated from *Borrelia burdorferi*, which protein comprises SEQ ID NO:1 or a fragment thereof having at least 10 consecutive amino acids, or SEQ ID NO:2 or a fragment thereof having at least 10 consecutive amino acids, or a nucleic acid fragment which hybridizes with the sequence and which has a length of at least 18 consecutive nucleotides;

subjecting the sample and nucleic acid sequence to polymerase chain reaction; and detecting the presence or absence of *Borrelia burgdorferi*.

* * * * *

SEQUENCE LISTING

<160> NUMBER OF SEQ ID NOS: 13

<210> SEQ ID NO 1
<211> LENGTH: 183
<212> TYPE: PRT
<213> ORGANISM: Borrelia burgdorferi

<400> SEQUENCE: 1

Met Lys Lys Phe Asn Leu Ile Ile Glu Ala Leu Phe Ala Ile Leu Leu
1               5                   10                  15

Thr Ala Cys Asn Phe Gly Leu Met Glu Glu Thr Lys Ile Ala Leu Glu
                20                  25                  30

Ser Ser Ser Lys Asp Val Lys Asn Lys Ile Leu Gln Ile Lys Lys Asp
            35                  40                  45

Ala Glu Asp Lys Gly Val Asn Phe Ala Ala Phe Thr Ser Ser Glu Thr
    50                  55                  60

Gly Ser Lys Val Thr Asn Gly Gly Leu Ala Leu Arg Glu Ala Lys Ile
65                  70                  75                  80

Gln Ala Ile Asn Glu Val Glu Lys Phe Leu Lys Arg Ile Glu Glu Glu
                85                  90                  95

Ala Leu Lys Leu Lys Glu His Gly Asn Ser Gly Gln Phe Leu Glu Leu
                100                 105                 110

Phe Asp Leu Leu Leu Glu Val Leu Glu Ser Leu Glu Pro Ile Gly Ile
            115                 120                 125

Lys Gly Leu Lys Asp Phe Ile Ser Glu Glu Ala Lys Cys Asn Pro Ile
130                 135                 140

Ser Thr Ser Glu Arg Leu Ile Glu Val Lys Val Gln Ile Glu Asn Lys
145                 150                 155                 160

Met Glu Glu Val Lys Arg Lys Gln Asn Leu Asn Lys Glu Arg Lys Ser
                165                 170                 175

Asn Lys Gly Lys Lys Lys Lys
            180

<210> SEQ ID NO 2
<211> LENGTH: 170
<212> TYPE: PRT
<213> ORGANISM: Borrelia burgdorferi

<400> SEQUENCE: 2

Met Ile Lys Tyr Asn Lys Ile Ile Leu Thr Leu Thr Leu Leu Ala Ser
1               5                   10                  15

Leu Leu Ala Ala Cys Ser Leu Thr Gly Lys Ala Arg Leu Glu Ser Ser
                20                  25                  30

Val Lys Asp Ile Thr Asn Glu Ile Glu Lys Ala Ile Lys Glu Ala Glu
            35                  40                  45

Asp Ala Gly Val Lys Thr Asp Ala Phe Thr Glu Thr Gln Thr Gly Gly
    50                  55                  60

Lys Val Ala Gly Pro Lys Ile Arg Ala Ala Lys Ile Arg Val Ala Asp
65                  70                  75                  80

Leu Thr Ile Lys Phe Leu Glu Ala Thr Glu Glu Thr Ile Thr Phe
                85                  90                  95

Lys Glu Asn Gly Ala Gly Glu Asp Glu Phe Ser Gly Ile Tyr Asp Leu
                100                 105                 110

Ile Leu Asn Ala Ala Lys Ala Val Glu Lys Ile Gly Met Lys Asp Met
            115                 120                 125

Thr Lys Thr Val Glu Glu Ala Ala Lys Glu Asn Pro Lys Thr Thr Ala
    130                 135                 140

Asn Gly Ile Ile Glu Ile Val Lys Val Met Lys Ala Lys Val Glu Asn
145                 150                 155                 160

Ile Lys Glu Lys Gln Thr Lys Asn Gln Lys
                165                 170

<210> SEQ ID NO 3
<211> LENGTH: 552
<212> TYPE: DNA
<213> ORGANISM: Borrelia burgdorferi

<400> SEQUENCE: 3

```
atgaaaaagt tcaatttaat aattgaggcg ctgtttgcta ttctattaac agcttgtaat      60
tttggattaa tggaagaaac aaaaatagcg cttgaatcat cctctaagga tgtaaaaaat     120
aaaattttac aaataaaaaa agacgctgag gacaagggtg taaattttgc agcttttaca     180
agcagtgaaa ccggttctaa agtgacaaat ggaggattag ctttaagaga agcaaaaata     240
caagcaatta atgaagtgga aaagtttctc aagagaatag aagaagaggc tttaaaactt     300
aaagaacatg gaaatagtgg tcaattcttg gagctgtttg acttactgct tgaagtttta     360
gaatcattag aaccgattgg aataaaaggc ttaaaagact ttatttcaga ggaagctaaa     420
tgtaacccta taagcacatc tgaaagatta attgaggtta aggtgcaaat agaaaataag     480
atggaagagg ttaagagaaa acaaaatctt aataaggaga gaaaaagtaa taaggcaaa      540
aaaaagaaat aa                                                        552
```

<210> SEQ ID NO 4
<211> LENGTH: 513
<212> TYPE: DNA
<213> ORGANISM: Borrelia burgdorferi

<400> SEQUENCE: 4

```
atgattaaat ataataaaat tatacttaca ctaactttac ttgctagcct gttagcagca      60
tgtagtttaa caggaaaagc tagattggaa tcatcagtta aagacattac aaatgaaata     120
gagaaagcta taaagaagc tgaagacgct ggtgtaaaga cagacgcgtt cacagaaaca     180
caaacaggtg gcaaggtggc aggccctaaa ataagagcag caaaaatacg cgtcgctgac     240
ttaacaatca aattcctaga agcaacagaa gaggaaacta ttcacatttaa agaaatgga     300
gcgggggaag atgaattctc aggaatatac gatttaatac tcaacgccgc aaaagcagta     360
gaaaaaattg ggatgaaaga tatgacaaaa acggtcgaag aggccgctaa agaaaatcct     420
aaaactacag ctaatgggat aattgagatt gtaaaagtaa tgaaagcaaa agtggaaaac     480
attaaagaaa aacaaactaa aaatcaaaaa taa                                  513
```

<210> SEQ ID NO 5
<211> LENGTH: 12
<212> TYPE: PRT
<213> ORGANISM: Borrelia burgdorferi

<400> SEQUENCE: 5

Thr Asp Ala Phe Thr Glu Thr Gln Thr Gly Gly Lys
 1               5                  10

<210> SEQ ID NO 6
<211> LENGTH: 8
<212> TYPE: PRT
<213> ORGANISM: Borrelia burgdorferi

<400> SEQUENCE: 6

Asp Ile Thr Asn Glu Ile Glu Lys
 1               5

<210> SEQ ID NO 7
<211> LENGTH: 13
<212> TYPE: PRT

<213> ORGANISM: Borrelia burgdorferi

<400> SEQUENCE: 7

Phe Leu Glu Ala Thr Glu Glu Glu Thr Ile Thr Phe Lys
1 5 10

<210> SEQ ID NO 8
<211> LENGTH: 35
<212> TYPE: DNA
<213> ORGANISM: Artificial Sequence
<220> FEATURE:
<223> OTHER INFORMATION: A primer

<400> SEQUENCE: 8
acwgatgcwt ttacwgarac wcaaacwggw ggwaa 35

<210> SEQ ID NO 9
<211> LENGTH: 23
<212> TYPE: DNA
<213> ORGANISM: Artificial Sequence
<220> FEATURE:
<223> OTHER INFORMATION: A primer

<400> SEQUENCE: 9
gatatwacwa aygaratwga raa 23

<210> SEQ ID NO 10
<211> LENGTH: 36
<212> TYPE: DNA
<213> ORGANISM: Artificial Sequence
<220> FEATURE:
<223> OTHER INFORMATION: A primer

<400> SEQUENCE: 10
tttttrgarg cwacwgarga rgaracwatw acwttt 36

<210> SEQ ID NO 11
<211> LENGTH: 37
<212> TYPE: DNA
<213> ORGANISM: Artificial Sequence
<220> FEATURE:
<223> OTHER INFORMATION: A primer

<400> SEQUENCE: 11
gagggatcca tcatgattaa atataataaa attatac 37

<210> SEQ ID NO 12
<211> LENGTH: 38
<212> TYPE: DNA
<213> ORGANISM: Artificial Sequence
<220> FEATURE:
<223> OTHER INFORMATION: A primer

<400> SEQUENCE: 12
gagggatcca tcatgaaaag tttaacagga aaagctag 38

<210> SEQ ID NO 13
<211> LENGTH: 36
<212> TYPE: DNA
<213> ORGANISM: Artificial Sequence
<220> FEATURE:
<223> OTHER INFORMATION: A primer

<400> SEQUENCE: 13
ggactgcagg tcgacttatt tttgattttt agtttg 36